US009700237B2

(12) United States Patent
Niemimaki (10) Patent No.: US 9,700,237 B2
(45) Date of Patent: Jul. 11, 2017

(54) ACCELERATION MEASUREMENT IN EXERCISE APPARATUS (71) Applicant: Polar Electro Oy, Kempele (FI)

(72) Inventor: Mika Niemimaki, Haukipudas (FI)

(73) Assignee: POLAR ELECTRO OY, Kempele (FI)

(*) Notice: Subject to any disclaimer, the term of this patent is extended or adjusted under 35 U.S.C. 154(b) by 180 days.

(21) Appl. No.: 13/781,212

(22) Filed: Feb. 28, 2013

(65) Prior Publication Data
US 2013/0237882 A1 Sep. 12, 2013

(30) Foreign Application Priority Data

Mar. 6, 2012 (FI) .................................. 20125239

(51) Int. Cl.
A61B 5/00 (2006.01)
A61B 5/11 (2006.01)
A61B 5/024 (2006.01)

(52) U.S. Cl.
CPC ............. A61B 5/11 (2013.01); A61B 5/4866 (2013.01); A61B 5/681 (2013.01); A61B 5/7278 (2013.01); A61B 5/02438 (2013.01); A61B 5/1118 (2013.01); A61B 5/6824 (2013.01); A61B 2560/0223 (2013.01); A61B 2562/0219 (2013.01)

(58) Field of Classification Search
None
See application file for complete search history.

(56) References Cited

U.S. PATENT DOCUMENTS

2008/0214360 A1 9/2008 Stirling et al.
2009/0015421 A1* 1/2009 Niva et al. ..................... 340/670
2011/0012759 A1* 1/2011 Yin .................................. 341/20

FOREIGN PATENT DOCUMENTS

EP 2 015 029 A1 1/2009
GB 2447647 A 9/2008
WO 2009112981 A1 9/2009

OTHER PUBLICATIONS

"Calibrate", http://www.merriam-webster.com/dictionary/calibrate, 4 pages, printed Jun. 23, 2016.*

(Continued)

Primary Examiner — Devin Henson
Assistant Examiner — Matthew Kremer
(74) Attorney, Agent, or Firm — Hoffmann & Baron, LLP (57) ABSTRACT An apparatus for measuring a physiological parameter of a user is disclosed. The apparatus comprises at least one processor and at least one memory comprising a computer program code comprising program instructions of a first algorithm modelling acquisition of the physiological parameter from motion of a user's arm and program instructions of a second algorithm modelling acquisition of the physiological parameter from motion of the user's torso. The at least one memory and the computer program code are configured, with the at least one processor, to cause the apparatus to: acquire torso acceleration data representing motion of the torso of the user; process the torso acceleration data with the second algorithm; and acquire, from the acceleration data processed with the second algorithm, reference parameters for the first algorithm.

16 Claims, 3 Drawing Sheets (56) References Cited

OTHER PUBLICATIONS

Prill, et al., "Simultaneous Assessment of Posture and Limb Movements (e.g., Periodic Leg Movements) with Calibrated Multiple Accelerometry," Physiol. Meas., pp. N47-N53, vol. 27:10 (Oct. 1, 2006).
Chen, et al., "Military Metabolic Monitoring. Predicting Energy Expenditure of Physical Activity Using Hip- and Wrist-Worn Accelerometers," Diabetes Technology & Therapeutics, pp. 1023-1033, vol. 5:6 (Dec. 1, 2003).
European Search Report, Application No. EP 13 15 4861, 2 pages, May 22, 2013.
Office Action, Finnish Application No. 20125239, dated Nov. 5, 2012; 1 page.

\* cited by examiner

ACCELERATION MEASUREMENT IN EXERCISE APPARATUS

CROSS-REFERENCE TO RELATED APPLICATION

This application claims priority based on Finnish Application No. 20125239, filed Mar. 6, 2012, which is incorporated herein by reference in its entirety.

BACKGROUND

Field

The invention relates to the field of exercise devices and, particularly, to determining a physiological parameter of a user from measured acceleration data.

Description of the Related Art

Conventional exercise apparatuses comprise sensors attached to a user's arm, torso, or foot and arranged to measure acceleration data. Various physiological parameters may be computed from the acceleration data, e.g. speed and energy expenditure. The acceleration data may be processed by a determined algorithm according to the attachment location of the sensor. The selection of the appropriate algorithm may be necessary, because a sensor attached to the user's arm experiences a different motion pattern than a sensor attached to the torso or the feet. A conventional solution is that each sensor is provided with a single dedicated algorithm for processing the acceleration data, and the selected dedicated algorithm also defines the attachment location.

SUMMARY

According to an aspect of the present invention, there is provided an apparatus comprising at least one processor and at least one memory comprising a computer program code. The computer program code comprises program instructions of a first algorithm modelling acquisition of a physiological parameter from motion of a user's arm and program instructions of a second algorithm modelling acquisition of the physiological parameter from motion of the user's torso. The at least one memory and the computer program code are configured, with the at least one processor, to cause the apparatus to: acquire torso acceleration data representing motion of the torso of the user; process the torso acceleration data with the second algorithm; and acquire, from the acceleration data processed with the second algorithm, reference parameters for the first algorithm.

Embodiments of the invention are defined in the dependent claims.

BRIEF DESCRIPTION OF THE DRAWINGS

Embodiments of the present invention are described below, by way of example only, with reference to the accompanying drawings, in which.

DETAILED DESCRIPTION

The following embodiments are exemplary. Although the specification may refer to "an", "one", or "some" embodiment(s) in several locations, this does not necessarily mean that each such reference is to the same embodiment(s), or that the feature only applies to a single embodiment. Single features of different embodiments may also be combined to provide other embodiments. Furthermore, words "comprising" and "including" should be understood as not limiting the described embodiments to consist of only those features that have been mentioned and such embodiments may contain also features/structures that have not been specifically mentioned.

Embodiments of the invention described herein relate to an apparatus comprised in a wrist device worn by a user in his/her wrist but it should be appreciated that the principles of the invention may be generalized to a device worn in the arm or in the hand of the user. The apparatus is configured to determine a physiological parameter of the user unobtrusively from acceleration data by using two different algorithms: one applied to acceleration data measured from arm motion and one applied to acceleration data measured from torso motion of the user.

Figure 1A:
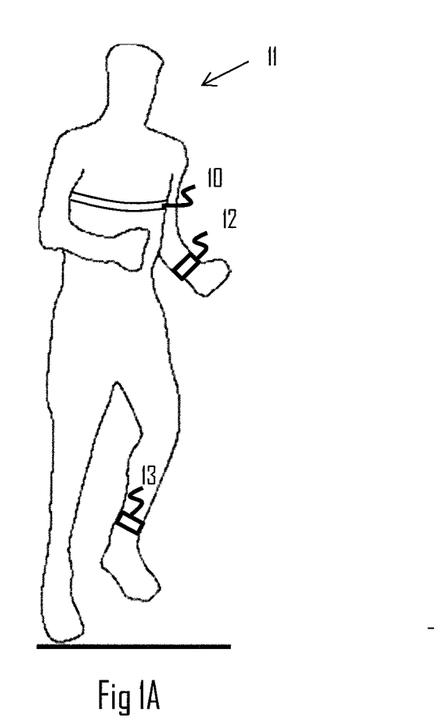
FIGS. 1A and 1B illustrate a performance monitoring system.
Figure 1B:
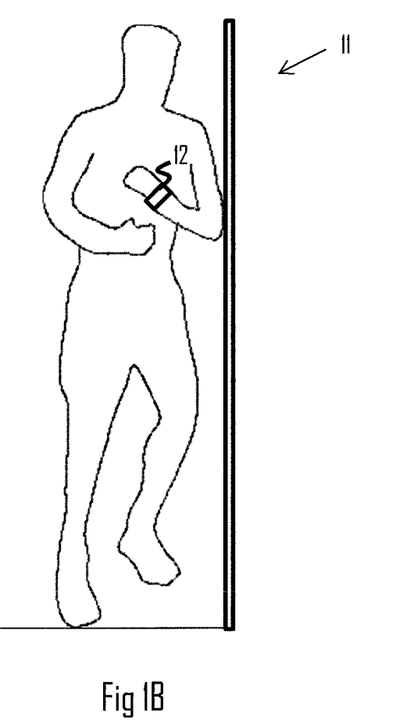

FIGS. 1A and 1B illustrate the user 11 wearing the wrist device 12 in his/her wrist. The wrist device 12 may be configured to monitor the user's 11 performance during an exercise, or it may be an activity monitor monitoring the user's 11 general activity during throughout the day. The wrist device 12 may carry out the monitoring autonomously or in cooperation with another exercise apparatus, e.g. a heart rate transmitter 10 attached to the user's 11 torso, for example. The heart rate transmitter 10 may be configured to measure the user's 11 heart rate, while the wrist device 12 may operate as the user interface apparatus. Additionally, the wrist device 12 may comprise at least one acceleration sensor be configured to measure motion of the wrist device 12, and the wrist device 12 may comprise algorithms for processing the physiological parameter from the measurement data produced by the at least one acceleration sensor. The acceleration sensor may comprise any inertia measurement device, e.g. a gyroscope and/or an accelerometer. The acceleration sensor measures its own motion, acceleration in terms of the rate of change in velocity, and converts the measured acceleration data into an electric signal. Acceleration can be expressed by the unit of measurement g. One g is the acceleration caused to an object by the earth's gravity. Accelerations between −16 to +16 g can usually be measured from human movement. Due to its implementation, the accelerometer may belong to microelectromechanical systems (MEMS). Various techniques may be used for measuring the acceleration. Piezo-resistor technology employs material whose resistance changes as it compresses. The acceleration of mass produces a force in a piezo resistor. If constant current is supplied through the piezo resistor, its voltage changes according to the compression caused by acceleration. In piezo-electric technology, a piezo-electric sensor generates charging when the sensor is accelerated. In a silicon bridge technology, a silicon chip is etched so that a silicon mass remains on it at the end of a silicon beam. When the acceleration is directed to the silicon chip, the silicon mass focuses a force on the silicon beam, thus changing the resistance of the silicon beam. Micromachined silicon technology is based on the use of a differential capacitor. Voice coil technology is based on the same principle as a microphone. Examples of suitable acceleration sensors comprise, among others: Analog Devices ADXL345, Pewatron HW or VTI Technologies SCA series. The implementation of the acceleration sensor may also be based on other appropriate techniques, for example on a gyroscope integrated into a silicon chip or on a micro vibration switch incorporated into a surface mounting component. It is also to be noted that the acceleration sensor may measure the acceleration in one, two or three dimensions. Instead of just one acceleration sensor, two or even three separate accelerometers each measuring a different dimension may be utilized.

Let us now consider the estimation of the physiological parameter first with reference to FIG. 1A. The acceleration data needed for computing the physiological parameter may in general be acquired from a sensor attached to any location in the user's 11 body. The location of the sensor defines also the algorithm that is applied to the acceleration data measured by the sensor. For example, the motion of the torso is very different from the motion of an arm or a foot when the user 11 runs or walks. The motion of the arm or the foot is dependent on the walking and/or running style of the user and, as known, different users adopt different walking/running styles. This introduces inaccuracy into the physiological parameter estimated from the acceleration data acquired from the sensor attached to the arm, e.g. comprised in the wrist device 12, or a sensor 13 attached to the foot. The motion of torso is, however, quite uniform and variances between different users are smaller. Thus, the estimation based on acceleration data measured by a sensor attached to the user's torso provides typically more accurate results. However, the device attached to the user's torso does not typically comprise a user interface and, therefore, the user is required to wear the wrist device 12, too.

Figure 2:
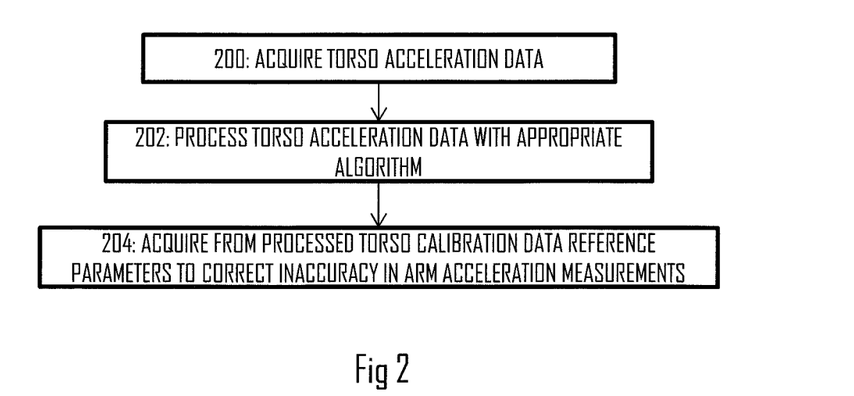
FIG. 2 is a flow diagram of a process for monitoring a user's physiological parameter according to an embodiment of the invention.

The present invention provides the apparatus comprised in the wrist device 12 and provided with the two above-mentioned algorithms: one processing torso acceleration measurement data and one processing arm acceleration measurement data. The apparatus may comprise at least one processor and at least one memory including program instructions of a first algorithm modelling acquisition of the physiological parameter from motion of the user's 11 arm and program instructions of a second algorithm modelling acquisition of the physiological parameter from motion of the user's 11 torso. The at least one memory and the computer program code are configured, with the at least one processor, to cause the apparatus to carry out a process for acquiring reference data for the estimation of the physiological parameter. FIG. 2 illustrates an embodiment of the process. Referring to FIG. 2, torso acceleration data representing motion of the user's 11 torso is acquired in block 200. In block 202, the torso acceleration data is processed with the second algorithm. In an embodiment, block 202 comprises estimating the physiological parameter with the second algorithm. In block 204, reference parameters for the first algorithm are acquired from the acceleration data processed with the second algorithm.

In the above-described embodiment, the inaccuracies of the first algorithm estimating the physiological parameter from the arm motion is corrected by using the reference parameters acquired as a result of the execution of the second, more accurate algorithm estimating the physiological parameter from the torso motion.

Referring to FIGS. 1A and 1B, the first algorithm may be executed during an operational phase whenever the user's arm moves back and forth as a part of conventional running or walking or, in other words, when the arm moves with respect to the torso (FIG. 1A). In the context of this document, let us define the arm in one aspect to comprise the user's arm from the elbow towards the hand and in another aspect to comprise also the upper arm from the elbow to the shoulder. On the other hand, the second algorithm may be executed during a calibration phase when the user 11 brings the wrist device 12 close to the torso such that the motion of the wrist device 12 is identical or substantially identical with the torso motion (FIG. 1B). The wrist device 12 may be brought into contact with the torso, but the contact should be interpreted in a broad sense since the wrist device 12 needs not be in direct contact with the torso as long as the motion of the wrist device 12 complies with the torso motion.

In an embodiment, the physiological parameter estimated from the acceleration data is speed. In an embodiment, the physiological parameter estimated from the acceleration data is energy expenditure. In an embodiment, the physiological parameter estimated from the acceleration data is the speed and the energy expenditure. The acceleration data may comprise a plurality of acceleration vectors, each acceleration vector representing an acceleration dimension in a spatial domain. One embodiment for estimating the speed from the acceleration vector is to compute an integral or average value of the acceleration vectors over a time domain. The acceleration vectors are periodic in the time domain, and they follow the rhythm of the user's 11 motion. Therefore, the integral or average may be computed over one or more periods in order to derive the user's overall speed and to negate those vectors that do not represent the overall motion of the user 11.

Figure 3:
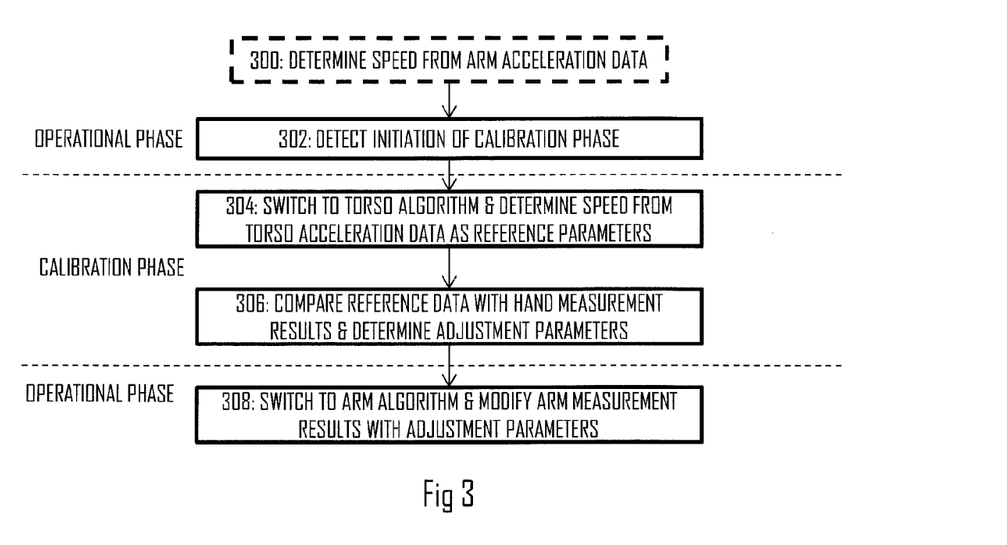
FIG. 3 is a flow diagram of a procedure for acquiring calibration values for an algorithm estimating a physiological parameter of the user.

Let us now consider the operation of the wrist device 12 during its operation with reference to FIG. 3. In this embodiment, the speed is used as an example of the physiological parameter. In block 300, the arm acceleration data is acquired and it is processed with the first algorithm adapted to the signal model of the arm acceleration data. As a result, a speed estimate is acquired and it may be presented to the user via a user interface and/or it may be stored in a memory unit. Block 300 is optional in the sense that a calibration phase may precede block 300.

In block 302, the apparatus detects initiation of the calibration phase. In an embodiment, the calibration phase is user-initiated and block 302 comprises reception of a user input via an input device of the wrist device 12, and the user input initiates the calibration phase. In another embodiment, the calibration phase is initiated by the apparatus in response to monitoring the wrist device 12 and detecting a determined event during the monitoring. In response to the detection of the event, the apparatus may start the calibration phase autonomously, or it may output a notification related to the initiation of the calibration phase via the user interface. The notification may be an instruction for the user to carry out the calibration phase, and the user may then trigger the calibration phase via a user input through the user interface. In an embodiment, the apparatus is configured to monitor the speed estimation carried out in block 300, and the event may be the detection that the estimated speed value is in a speed range where calibration is needed, e.g. because no calibration for the speed range has been made or that the speed estimated is detected to be inaccurate. The inaccuracy may be detected by monitoring the performance of the first algorithm, e.g. by monitoring variance in the estimate or by correlating estimates provided by the first algorithm at different times for similar acceleration data. Upon detecting that the variance is above a variance threshold and/or that the correlation is below than a correlation threshold, the calibration phase may be initiated.

In yet another embodiment, the apparatus is configured to monitor the location of the wrist device 12 with respect to the user's 11 torso. This may comprise monitoring whether the wrist device 12 is detached from the torso or in contact with the torso, and it be carried out, for example, by monitoring the acceleration vectors. When the wrist device 12 is in contact with the torso, an acceleration vector having a direction along the user's arm typically diminishes or becomes very small. On the other hand, when the wrist device 12 is detached from the torso and moves according to the motion of the user's arm during normal running, this acceleration vector is stronger. Therefore, the apparatus may compare the value of the acceleration vector with a threshold value, and when the value is lower than the threshold, the calibration phase may be initiated autonomously in the apparatus. In another embodiment, it is assumed that the user wears the heart rate transmitter 10 or similar chest-worn device attached to the user's torso, and the wrist device 12 is provided with a proximity detector configured to detect the proximity of the chest-worn device 10 through magnetic interaction between the wrist device and the chest-worn device 10, for example. Other mechanisms for detecting the presence of the wrist device 12 close to the user's torso are equally possible.

In yet another embodiment, the apparatus is configured to monitor the signal model of the acceleration data. The apparatus may correlate the signal model with a reference signal model representing a signal model associated with the motion of the user's arm and with a reference signal model representing a signal model associated with the motion of the user's torso. As a result, the apparatus acquires information on the similarity between the signal model of the acceleration data and the reference signal models, and the apparatus is configured to determine which one of the reference signal models match better with the acceleration data, e.g. which one of the correlations results in a higher correlation value. When the correlation with the reference signal model associated with the motion of the user's torso provides a higher correlation value, the apparatus may initiate or maintain the calibration phase. Otherwise, the apparatus may initiate or maintain the operational phase.

Upon detecting the initiation of the calibration phase in block 302, the apparatus starts the calibration phase and switches from the first algorithm to the second algorithm modelling the torso motion and starts to determine the speed with the second algorithm in block 304. The second algorithm may use only acceleration data acquired after the calibration phase was started. The reference parameters may comprise at least one speed estimate acquired as a result of the second algorithm.

In block 306, the reference data is compared with the results acquired with the first algorithm so as to determine the difference between the estimate of the first algorithm and the reference parameters. Block 306 may comprise comparing the speed estimated by the first algorithm with the speed estimated by the second algorithm. In an embodiment, block 306 comprises computing a difference between the speed estimated by the first algorithm and the speed estimated by the second algorithm. In another embodiment, block 306 comprises computing a ratio between the speed estimated by the first algorithm and the speed estimated by the second algorithm. As a result, adjustment parameters are acquired, the adjustment parameters being proportional to the difference between the speed estimated by the first algorithm and the speed estimated by the second algorithm. The speed estimated by the second algorithm is assumed to be an accurate estimate and, therefore, the speed estimated by the first algorithm is modified with the adjustment parameters. The assumption is that the user's actual speed remains constant over both speed estimates.

When the speed estimation with the second algorithm has been carried out and the adjustment parameters have been determined, the calibration phase may be ended, and the apparatus may switch to the operational phase. In block 308, the used algorithm is switched from the second algorithm to the first algorithm, and the speed estimates of the first algorithm are modified with the adjustment parameters. The modification may comprise scaling and/or offsetting the speed estimates of the first algorithm with the adjustment parameters or, in general, it may comprise mapping the speed estimate to a new speed estimate.

Figure 4:
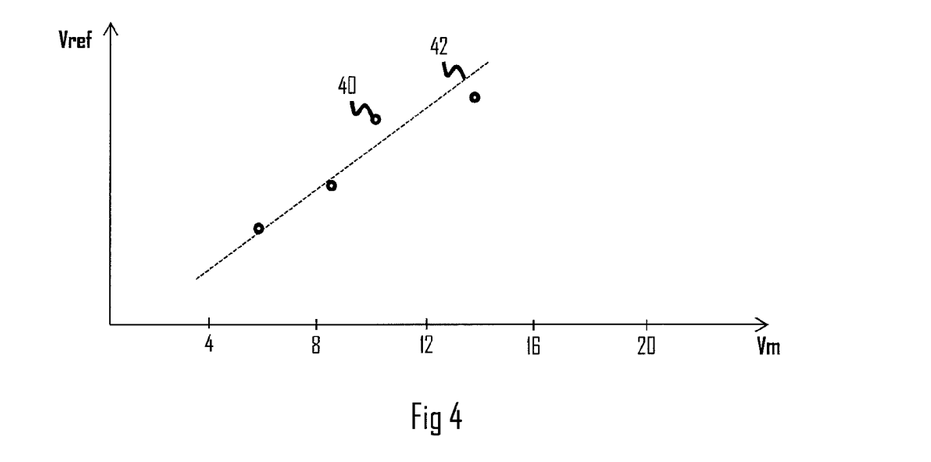
FIG. 4 illustrates an example of a calibration model according to an embodiment of the invention.

The apparatus may determine the adjustment parameters on the basis of available reference data, e.g. the reference speed values measured for different speeds with the second algorithm from the torso motion. FIG. 4 represents a graph mapping the measured speed Vm estimated with the first algorithm to the reference speed Vref measured with the second algorithm. Each dot, e.g. dot 40, represents a reference parameter acquired during one or more calibration phases. The apparatus may be configured to determine the adjustment parameters from a single reference parameter acquired during a calibration phase. In an embodiment, the apparatus computes the difference between the measured speed Vm and the reference speed Vref functioning as the reference parameter in order to determine an offset value from the difference. Any measured speed may then be offset with this offset value which functions as the adjustment parameter. The offsetting may comprise adding/subtracting the offset value to/from the measured speed measured during the operational phase. Herein, it is assumed that the measured speed Vm and the reference speed Vref have been computed when the user moves at a constant speed. In an embodiment, the apparatus uses as the measured speed Vm the latest value acquired with the first algorithm before the calibration phase was initiated, while the reference speed is acquired during the calibration phase. In another embodiment, the apparatus computes the ratio between the measured speed Vm and the reference speed Vref in order to determine a scaling value from the difference. Any measured speed may then be scaled with this offset value which functions as the adjustment parameter. The scaling may comprise multiplying the scaling value with the measured speed Vm measured during the operational phase. The same adjustment parameters may be applied to any value of the measured speed Vm, e.g. to the measured speed Vm at or around the speed for which the calibration phase has been carried out but also to the measured speed Vm measured further away from the speed for which the calibration phase has been carried out.

The apparatus may improve the accuracy of the adjustment parameters by carrying out the calibration phase for a plurality of different ranges or values of the measured physiological parameter, e.g. the speed as in the embodiment of FIG. 4. As shown by the dots in FIG. 4, the calibration phase may be carried out for a plurality of different speeds, e.g. six kilometers per hour (km/h), nine km/h, ten km/p (dot 40), and 14 km/h. As a consequence, a plurality of reference parameters is acquired, wherein the inter-relation between the measured values Vm and the reference values Vref form a regression model. This regression model improves the accuracy of the error of the first algorithm, as regression model represents the error for the plurality of measured values Vm. The apparatus may be configured to compute a calibration curve 42 from the regression model, e.g. by using a least squares fitting or another fitting. The fitting may comprise computation of the above-mentioned scaling value and/or offset value that represent the linear calibration curve 42 shown in FIG. 4. The calibration curve shows the mapping between the speed estimated with the first algorithm and the more accurate speed estimated with the second algorithm. The calibration curve may thus be used to improve the accuracy of the speed estimates of the first algorithm. During the operational phase, the calibration curve 42 may then be used to map the measured speed Vm to the corrected speed.

In other embodiments, the calibration curve is replaced by look-up table values, wherein the look-up table values may comprise the speeds for which the calibration has been carried out, e.g. the dots in FIG. 4. The speed measured during the operational phase may be modified with the adjustment parameters that have been computed to the speed closes to the measured speed. For example, if the speed measured with the first algorithm during the operational phase is 8 km/h, the adjustment parameters computed for the 9 km/h (FIG. 4) may be used to modify the speed estimate.

In the above-described embodiments, the acceleration data is acquired from the acceleration sensor(s) comprised in the wrist device 12. The arm acceleration data represents the acceleration data acquired during the operational phase, while the torso acceleration data represents the acceleration data acquired during the calibration phase. The arm acceleration data and the torso acceleration data may be measured by the same acceleration sensor(s), and it may be processed with the suitable algorithm depending on the phase.

Figure 5:
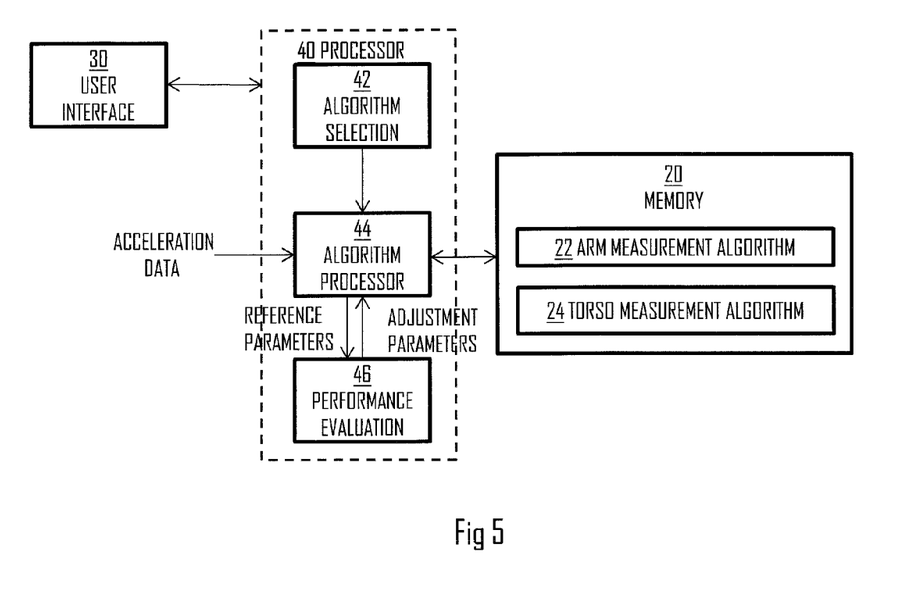
FIG. 5 illustrates a block diagram of an apparatus according to an embodiment of the invention.

Let us now consider an embodiment of the apparatus with reference to FIG. 5. As mentioned above, the apparatus may be comprised in the wrist device 12. It may be the wrist device 12 or it may form a part of the wrist device 12. For that purpose, the apparatus may comprise an attachment mechanism arranged to attach the apparatus to the user's wrist or arm. The attachment mechanism may comprise a strap. The apparatus comprises at least one processor 40 or a processing circuitry 40 and at least one memory 20. The memory may store program instructions 22 of the first algorithm modelling acquisition of the physiological parameter from motion of the user's arm. In FIG. 5, the first algorithm is called an arm measurement algorithm. The memory may further store program instructions of the second algorithm modelling acquisition of the physiological parameter from the motion of the user's torso. In FIG. 5, the second algorithm is called a torso measurement algorithm. The memory 20 may further store computer program code configuring the operation of the processor 40 in the above-described manner. As a consequence, the at least one memory 20 and the computer program code are configured, with the at least one processor 40, to cause the apparatus to acquire torso acceleration data representing motion of a torso of a user; process the torso acceleration data with the second algorithm; and acquire, from the acceleration data processed with the second algorithm, the reference parameters for the first algorithm.

The processor 40 may comprise an algorithm selection circuitry 42 configured to select the first algorithm or the second algorithm. The selection may be based on the detection of the current phase: the calibration phase or the operational phase. Upon detecting the initiation of the calibration phase, the algorithm selection circuitry 42 may instruct an algorithm processor circuitry 44 to retrieve from the memory the torso measurement algorithm (the second algorithm) and to process the acquired measurement data with the torso measurement algorithm in order to derive the reference parameter(s). The algorithm processor circuitry 44 may then be configured to output the reference parameter(s) to a performance evaluation circuitry 46 configured to compare the reference parameter(s) with the measured physiological parameters acquired as a result of the execution of the first algorithm and to derive the adjustment parameters in the above-described manner. If the measured physiological parameters are not available yet, e.g. if the calibration phase is carried out before any operational phase, the performance evaluation may store the reference parameter(s) and, upon acquiring the measured physiological parameters during a subsequent operational phase, the performance evaluation circuitry 46 may derive and output the adjustment parameters. Upon receiving the adjustment parameters, the algorithm processor circuitry 44 may then modify the measured physiological parameters acquired during the operational phase with the adjustment parameters and thus acquire the corrected physiological parameters.

Upon detecting the initiation of the operational phase, the algorithm selection circuitry 42 may instruct the algorithm processor circuitry 44 to retrieve from the memory the arm measurement algorithm (the first algorithm) and to process the acquired measurement data with the arm measurement algorithm in order to derive the measured physiological parameters. The algorithm processor circuitry 44 may modify the measured physiological parameters with the adjustment parameters and thus acquire the corrected physiological parameters.

In an embodiment, the actual modification of the measured physiological parameters acquired during the operational phase is performed outside the apparatus, e.g. in a computer or a server to which the apparatus is arranged to output the measured physiological parameters and the reference parameters. In such embodiments, the apparatus is nevertheless configured to acquire the reference parameters in the above-described manner.

The apparatus may further comprise a user interface 30 comprising an input device comprising one or more buttons or keys. The user interface may also comprise an output device comprising a display and/or a loudspeaker. The algorithm selection circuitry may operate in connection with the user interface in order to receive the user input triggering the calibration phase or to output a notification suggesting or indicating the initiation of the calibration phase that instructs the user to put the wrist device close to the user's torso. The algorithm processor circuitry 44 may be configured to display the measured physiological parameters modified with the adjustment parameters to the user via the user interface 30. For example, the algorithm processor circuitry 44 may be configured to estimate the speed and to output the estimated speed through the user interface 30.

The apparatus may further comprise at least one acceleration sensor configured to measure the acceleration data and output the acceleration data to the processor 40. The apparatus may further comprise a battery to provide the apparatus with a power supply. The apparatus may further comprise an input/output interface to provide the apparatus with wired and/or wireless communication capability in order to output the measured physiological parameters and/or to receive any measurement results, e.g. from the heart rate transmitter 10 attached to the user's 11 torso.

As used in this application, the term 'circuitry' refers to all of the following: (a) hardware-only circuit implementations such as implementations in only analog and/or digital circuitry; (b) combinations of circuits and software and/or firmware, such as (as applicable): (i) a combination of processor(s) or processor cores; or (ii) portions of processor(s)/software including digital signal processor(s), software, and at least one memory that work together to cause an apparatus to perform specific functions; and (c) circuits, such as a microprocessor(s) or a portion of a microprocessor(s), that require software or firmware for operation, even if the software or firmware is not physically present.

This definition of 'circuitry' applies to all uses of this term in this application. As a further example, as used in this application, the term "circuitry" would also cover an implementation of merely a processor (or multiple processors) or portion of a processor, e.g. one core of a multi-core processor, and its (or their) accompanying software and/or firmware. The term "circuitry" would also cover, for example and if applicable to the particular element, a baseband integrated circuit, an application-specific integrated circuit (ASIC), and/or a field-programmable grid array (FPGA) circuit for the apparatus according to an embodiment of the invention.

The processes or methods described in connection with FIGS. 2 to 4 may also be carried out in the form of a computer process defined by a computer program. The computer program may be in source code form, object code form, or in some intermediate form, and it may be stored in some sort of carrier, which may be any entity or device capable of carrying the program. Such carriers include transitory and/or non-transitory computer media, e.g. a record medium, computer memory, read-only memory, electrical carrier signal, telecommunications signal, and software distribution package. Depending on the processing power needed, the computer program may be executed in a single electronic digital processing unit or it may be distributed amongst a number of processing units.

It will be obvious to a person skilled in the art that, as technology advances, the inventive concept can be implemented in various ways. The invention and its embodiments are not limited to the examples described above but may vary within the scope of the claims.

What is claimed is:

1. An apparatus comprising:
    at least one processor;
    an acceleration sensor;
    a wrist apparatus capable of attaching the acceleration sensor to a user's wrist or arm, the acceleration sensor providing torso acceleration data and arm acceleration data to the at least one processor; and
    at least one memory comprising a computer program code comprising program instructions of a first algorithm applicable to the arm acceleration data measured from motion of the user's arm program instructions of a second algorithm different from the first algorithm and applicable to the torso acceleration data measured from motion of the user's torso, wherein the at least one memory and the computer program code are configured, with the at least one processor, to cause the apparatus to perform operations comprising:
    acquiring, using the acceleration sensor, the torso acceleration data from the torso of the user while the acceleration sensor is held close to the torso of the user such that motion of the acceleration sensor is identical to the motion of the user's torso;
    detecting, by the processor from the acquired torso acceleration data that the acquired torso acceleration data represents the motion of the user's torso and, as a response to said detecting from the acquired torso acceleration data, using the second algorithm to process the acquired torso acceleration data acquired from the acceleration sensor and to provide processed torso acceleration data;
    acquiring reference parameters from the processed torso acceleration data;
    acquiring, using the acceleration sensor, the arm acceleration data from the arm of the user while the acceleration sensor is not held close to the torso of the user such that the motion of the acceleration sensor is not identical to the motion of the user's torso;
    detecting, by the processor from the acquired arm acceleration data that the acquired arm acceleration data represents the motion of the user's arm and, as a response to said detecting from the acquired arm acceleration data, using the first algorithm to process the arm acceleration data acquired from the acceleration sensor and to provide processed arm acceleration data;
    calibrating the processed arm acceleration data using the reference parameters from the processed torso acceleration data to acquire a calibrated value of a physiological parameter, wherein the physiological parameter comprises speed of the user; and
    causing the calibrated value of the physiological parameter to be displayed.

2. The apparatus of claim 1, wherein the at least one memory and the computer program code are configured, with the at least one processor, to cause the apparatus to perform operations further comprising a triggering operation of the second algorithm by a user input.

3. The apparatus of claim 1, wherein the at least one memory and the computer program code are configured, with the at least one processor, to cause the apparatus to perform operations further comprising:
    detecting that the wrist apparatus has been brought into contact with the user's torso; and
    triggering the acquisition of the torso acceleration data and the use of the second algorithm in response to detecting that the wrist apparatus has been brought into contact with the user's torso.

4. The apparatus of claim 3, wherein the at least one memory and the computer program code are configured, with the at least one processor, to perform operations comprising causing the apparatus to determine a position of the wrist apparatus with respect to the user's torso from the acquired torso acceleration data.

5. The apparatus of claim 4, wherein the processed arm acceleration data is associated with an acceleration vector representing an acceleration direction along the user's arm; and
    wherein the at least one memory and the computer program code are configured, with the at least one processor, to perform operations comprising: causing the apparatus to evaluate the processed arm acceleration data associated with the acceleration vector representing the acceleration direction along the user's arm; and determining a position of the wrist apparatus from the acceleration vector.

6. The apparatus of claim 1, wherein the at least one memory and the computer program code are configured, with the at least one processor, to perform operations comprising:
    causing the apparatus to output, before the calibration, an uncalibrated value of the physiological parameter.

7. The apparatus of claim 1, wherein the apparatus further comprises a user interface, and wherein the at least one memory and the computer program code are configured, with the at least one processor, to perform operations comprising:

causing the apparatus to monitor a performance of the first algorithm; and     upon determining that the performance of the first algorithm is below a threshold, outputting an indication through the user interface to suggest the calibration.

8. The apparatus of claim 1, wherein the wrist apparatus is attachable to the user's wrist.

9. The apparatus of claim 8, the wrist apparatus further comprising an attachment mechanism comprising a strap, the attachment mechanism configured to attach the wrist apparatus to the user's wrist or arm.

10. An apparatus comprising:

at least one processor;

a wrist apparatus capable of attaching the at least one processor to a user's wrist or arm; and     at least one memory comprising a computer program code comprising program instructions of a first algorithm applicable to arm acceleration data measured from motion of the user's arm and program instructions of a second algorithm different from the first algorithm and applicable to torso acceleration data measured from motion of the user's torso, wherein the at least one memory and the computer program code are configured, with the at least one processor, to cause the apparatus to perform operations comprising:

acquiring, using an acceleration sensor, the torso acceleration data from the torso of the user while the acceleration sensor is held close to the torso of the user such that motion of the acceleration sensor is identical to the motion of the user's torso;

detecting, by the processor from the acquired torso acceleration data that the acquired torso acceleration data represents the motion of the user's torso and, as a response to said detecting from the acquired torso acceleration data, using the second algorithm to process the acquired torso acceleration data acquired from the acceleration sensor and to provide processed torso acceleration data;

acquiring reference parameters from the processed torso acceleration data;

acquiring, using the acceleration sensor, the arm acceleration data from the arm of the user while the acceleration sensor is not held close to the torso of the user such that the motion of the acceleration sensor is not identical to the motion of the user's torso;

detecting, by the processor from the acquired arm acceleration data that the acquired arm acceleration data represents the motion of the user's arm and, as a response to said detecting from the acquired arm acceleration data, using the first algorithm to process the arm acceleration data acquired from the acceleration sensor and to provide processed arm acceleration data;

calibrating the processed arm acceleration data using the reference parameters from the processed torso acceleration data to acquire a calibrated value of a physiological parameter, wherein the physiological parameter comprises speed of the user; and     causing the calibrated value of the physiological parameter to be displayed.

11. The apparatus of claim 10, wherein the at least one memory and the computer program code are configured, with the at least one processor, to cause the apparatus to perform operations further comprising a triggering operation of the second algorithm by a user input.

12. The apparatus of claim 10, wherein the at least one memory and the computer program code are configured, with the at least one processor, to cause the apparatus to perform operations further comprising:

detecting that the wrist apparatus has been brought into contact with the user's torso; and     triggering the acquisition of the torso acceleration data and the use of the second algorithm in response to detecting that the wrist apparatus has been brought into contact with the user's torso.

13. The apparatus of claim 12, wherein the at least one memory and the computer program code are configured, with the at least one processor, to perform operations comprising causing the apparatus to determine a position of the wrist apparatus with respect to the user's torso from the acquired torso acceleration data.

14. The apparatus of claim 12, wherein the processed arm acceleration data is associated with an acceleration vector representing an acceleration direction along the user's arm, and     wherein the at least one memory and the computer program code are configured, with the at least one processor, to perform operations comprising causing the apparatus to evaluate the processed arm acceleration data associated with the acceleration vector representing the acceleration direction along the user's arm and to determine a position of the wrist apparatus from the acceleration vector.

15. The apparatus of claim 10, wherein the at least one memory and the computer program code are configured, with the at least one processor, to perform operations comprising:

causing the apparatus to output, before the calibration, an uncalibrated value of the physiological parameter.

16. The apparatus of claim 10, wherein the apparatus further comprises a user interface, and wherein the at least one memory and the computer program code are configured, with the at least one processor, to perform operations comprising:

causing the apparatus to monitor a performance of the first algorithm; and     upon determining that the performance of the first algorithm is below a threshold, outputting an indication through the user interface to suggest the calibration.

* * * * *

UNITED STATES PATENT AND TRADEMARK OFFICE
CERTIFICATE OF CORRECTION

| | |
|---|---|
| PATENT NO. | : 9,700,237 B2 |
| APPLICATION NO. | : 13/781212 |
| DATED | : July 11, 2017 |
| INVENTOR(S) | : Niemimaki |

Page 1 of 1

It is certified that error appears in the above-identified patent and that said Letters Patent is hereby corrected as shown below:

In the Specification

Column 2, Line 32:  now reads "activity during throughout the day."
should read -- activity throughout the day. --

Column 6, Line 61:  now reads "ten km/p"
should read -- ten km/h --

Signed and Sealed this
Twenty-seventh Day of February, 2018

Andrei Iancu
*Director of the United States Patent and Trademark Office*